United States Patent
Matsumoto et al.

(10) Patent No.: US 12,016,732 B2
(45) Date of Patent: Jun. 25, 2024

(54) PUNCTURE NEEDLE, ULTRASOUND DIAGNOSTIC APPARATUS, AND CONTROL METHOD OF ULTRASOUND DIAGNOSTIC APPARATUS

(71) Applicant: FUJIFILM Corporation, Tokyo (JP)

(72) Inventors: Tsuyoshi Matsumoto, Kanagawa (JP); Tomoki Inoue, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 176 days.

(21) Appl. No.: 17/355,473

(22) Filed: Jun. 23, 2021

(65) Prior Publication Data

US 2021/0315547 A1 Oct. 14, 2021

Related U.S. Application Data

(63) Continuation of application No. PCT/JP2019/035306, filed on Sep. 9, 2019.

(30) Foreign Application Priority Data

Jan. 17, 2019 (JP) .................................. 2019-006254

(51) Int. Cl.
*A61B 8/00* (2006.01)
*A61B 8/08* (2006.01)
(Continued)

(52) U.S. Cl.
CPC .............. *A61B 8/54* (2013.01); *A61B 8/0841* (2013.01); *A61B 8/461* (2013.01); *A61B 8/5215* (2013.01);
(Continued)

(58) Field of Classification Search
CPC ......... A61B 8/54; A61B 8/0841; A61B 8/461; A61B 8/5215; A61B 8/5223;
(Continued)

(56) References Cited

U.S. PATENT DOCUMENTS

| 4,582,061 A | 4/1986 | Fry |
| 2006/0247530 A1 | 11/2006 | Hardin et al. |

(Continued)

FOREIGN PATENT DOCUMENTS

| CN | 104414686 A | 3/2015 |
| CN | 105101882 A | 11/2015 |

(Continued)

OTHER PUBLICATIONS

International Search Report issued in PCT/JP2019/035306; mailed Nov. 19, 2019.

(Continued)

*Primary Examiner* — Katherine L Fernandez
*Assistant Examiner* — Brooke Lyn Klein
(74) *Attorney, Agent, or Firm* — Studebaker & Brackett PC

(57) ABSTRACT

A puncture needle includes a shaft-part, a needle-tip-part disposed at a tip of the shaft-part, and processed-parts that are arranged on an outer peripheral part of the shaft-part along a length direction of the shaft-part and form an arithmetic progression in which arrangement intervals gradually decrease toward the needle-tip-part, wherein among the processed-parts, an arrangement interval between a first-processed-part which is separated from the needle-tip-part by a predetermined distance and is closest to the needle-tip-part and a second-processed-part which is second closest to the needle-tip-part is equal to or less than a tolerance of the arithmetic progression, or a distance from the needle-tip-part to the first-processed-part which is closest to the needle-tip-part is equal to or less than the tolerance of the arithmetic progression and equal to a difference between the arrangement interval between the first-processed-part and the second-processed-part which is second closest to the needle-tip-part and the tolerance.

16 Claims, 8 Drawing Sheets

(51) Int. Cl.
  *A61B 17/34* (2006.01)
  *A61B 34/20* (2016.01)
  *A61B 90/00* (2016.01)

(52) U.S. Cl.
  CPC .... *A61B 8/5223* (2013.01); *A61B 2017/3413* (2013.01); *A61B 2034/2065* (2016.02); *A61B 2090/378* (2016.02)

(58) Field of Classification Search
  CPC ...... A61B 2034/2065; A61B 2090/378; A61B 2017/3413
  See application file for complete search history.

(56) References Cited

U.S. PATENT DOCUMENTS

| | | | |
|---|---|---|---|
| 2012/0165658 A1* | 6/2012 | Shi | A61B 5/06 600/424 |
| 2012/0253297 A1* | 10/2012 | Matsuzawa | A61M 5/329 604/272 |
| 2014/0213892 A1* | 7/2014 | Taylor | A61B 34/20 600/424 |
| 2014/0265024 A1 | 9/2014 | Quearry | |
| 2014/0336687 A1 | 11/2014 | Iwase et al. | |
| 2015/0065881 A1 | 3/2015 | Cho et al. | |
| 2016/0015361 A1 | 1/2016 | Osawa | |
| 2017/0020562 A1 | 1/2017 | Erkamp et al. | |

FOREIGN PATENT DOCUMENTS

| | | |
|---|---|---|
| CN | 107224317 A | 10/2017 |
| JP | 2011-125632 A | 6/2011 |
| JP | 2013-027513 A | 2/2013 |
| JP | 2013-116288 A | 6/2013 |
| JP | 5635462 B2 | 12/2014 |
| JP | 2016-516469 A | 6/2016 |
| WO | 2018/054969 A1 | 3/2018 |

OTHER PUBLICATIONS

Written Opinion issued in PCT/JP2019/035306; mailed Nov. 19, 2019.

The extended European search report issued by the European Patent Office on Feb. 22, 2022, which corresponds to European Patent Application No. 1990972.3-1126 and is related to U.S Appl. No. 17/355,473.

An Office Action mailed by China National Intellectual Property Administration on Nov. 15, 2023, which corresponds to Chinese Patent Application No. 201980089313.X and is related to U.S. Appl. No. 17/355,473; with English language translation.

* cited by examiner

PUNCTURE NEEDLE, ULTRASOUND DIAGNOSTIC APPARATUS, AND CONTROL METHOD OF ULTRASOUND DIAGNOSTIC APPARATUS

CROSS-REFERENCE TO RELATED APPLICATIONS

This application is a Continuation of PCT International Application No. PCT/JP2019/035306 filed on Sep. 9, 2019, which claims priority under 35 U.S.C § 119(a) to Japanese Patent Application No. 2019-006254 filed on Jan. 17, 2019. Each of the above application(s) is hereby expressly incorporated by reference, in its entirety, into the present application.

BACKGROUND OF THE INVENTION

1. Field of the Invention

The present invention relates to a puncture needle, an ultrasound diagnostic apparatus that detects a puncture needle inserted into a subject, and a control method of the ultrasound diagnostic apparatus.

2. Description of the Related Art

There is a technique of inserting a so-called puncture needle into a subject in order to place a catheter in the subject. In recent years, a method of inserting a puncture needle into a subject while observing the puncture needle inserted into the subject using an ultrasound diagnostic apparatus is often used.

In general, the ultrasound diagnostic apparatus comprises an ultrasound probe provided with a transducer array in which a plurality of elements are arranged. In a state where the ultrasound probe is brought into contact with a body surface of the subject, an ultrasound beam is transmitted from the transducer array toward an inside of the subject, and an ultrasound echo from the subject is received by the transducer array to obtain element data. Further, the ultrasound diagnostic apparatus electrically processes the obtained element data to generate an ultrasound image for a relevant part of the subject.

Here, since the puncture needle is usually inserted in an inclined state with respect to the body surface of the subject, the ultrasound echo reflected from the puncture needle in the subject is difficult to propagate toward the ultrasound probe, and the puncture needle is sometimes not clearly depicted in the ultrasound image. Therefore, in order to clearly depict the puncture needle in the ultrasound image, for example, as disclosed in JP2011-125632A, a puncture needle which is processed to reflect an ultrasound beam from an ultrasound probe has been developed. A plurality of grooves for reflecting an ultrasound beam are formed on an outer peripheral part of the puncture needle of JP2011-125632A. In a case where the puncture needle of JP2011-125632A is inserted into a subject and the inserted puncture needle is irradiated with an ultrasound beam, the ultrasound beam applied to the puncture needle is reflected by the plurality of grooves formed in the puncture needle and propagates toward the ultrasound probe. Thus, the plurality of grooves formed in the puncture needle are depicted in the ultrasound image. In addition, as disclosed in JP5635462B, a position of a puncture needle may be confirmed by providing a light absorbing portion on a part of a surface of the puncture needle.

SUMMARY OF THE INVENTION

However, since a groove cannot be formed at a tip part of a sharply pointed puncture needle, a user such as a doctor cannot clearly grasp the tip part of the puncture needle even by observing an ultrasound image depicting a plurality of grooves of the puncture needle, and therefore, it is sometimes difficult to guide the tip part of the puncture needle to a desired place.

In addition, the groove of the puncture needle on the ultrasound image is sometimes concealed or disappears due to a high-intensity reflection signal, an acoustic shadow, or the like derived from a tissue in a subject. Thus, a position of the groove in the puncture needle is not specified, and it is sometimes difficult for the user to estimate a position of the tip part of the puncture needle. In addition, in a case where the light absorbing portion is provided on the part of the surface of the puncture needle as in JP5635462B, a cost of the puncture needle is increased.

The present invention has been made to solve such a conventional problem, and an object of the present invention is to provide a puncture needle, an ultrasound diagnostic apparatus, and a control method of the ultrasound diagnostic apparatus, with which a user can accurately grasp a tip part of the puncture needle.

In order to achieve the above object, a puncture needle according to a first aspect of the present invention comprises a shaft part, a needle tip part disposed at a tip of the shaft part, and a plurality of processed parts that are arranged on an outer peripheral part of the shaft part along a length direction of the shaft part and form an arithmetic progression in which arrangement intervals gradually decrease toward the needle tip part, in which among the plurality of processed parts, an arrangement interval between a first processed part which is separated from the needle tip part by a predetermined distance and is closest to the needle tip part and a second processed part which is second closest to the needle tip part is equal to or less than a tolerance of the arithmetic progression, or a distance from the needle tip part to the first processed part which is closest to the needle tip part is equal to or less than the tolerance of the arithmetic progression and equal to a difference between the arrangement interval between the first processed part and the second processed part which is second closest to the needle tip part and the tolerance.

It is preferable that the plurality of processed parts are grooves formed to surround a periphery of the shaft part.

An ultrasound diagnostic apparatus according to a second aspect of the present invention comprises a display unit that displays an ultrasound image in which the puncture needle is captured, an arrangement interval detection unit that recognizes the plurality of processed parts of the puncture needle and detects the arrangement intervals of the plurality of processed parts by image analysis of the ultrasound image, an arithmetic progression determination unit that determines whether or not the arrangement intervals of the plurality of processed parts detected by the arrangement interval detection unit form the arithmetic progression, a first processed part detection unit that calculates the tolerance of the arithmetic progression and detects the first processed part which is closest to the needle tip part among the plurality of processed parts based on the tolerance in a case where the arithmetic progression determination unit determines that the arithmetic progression is formed, and a needle tip part position estimation unit that estimates a position of the needle tip part based on a position of the first processed part detected by the first processed part detection unit.

Here, the needle tip part position estimation unit may estimate a point extending from the first processed part to a tip side of the shaft part by the predetermined distance as the position of the needle tip part in a case where the arrangement interval between the first processed part and the second processed part of the puncture needle is equal to or less than the tolerance of the arithmetic progression, and estimate a point extending from the first processed part to the tip side of the shaft part by the difference between the arrangement interval between the first processed part and the second processed part and the tolerance as the position of the needle tip part in a case where the distance from the needle tip part to the first processed part of the puncture needle is equal to or less than the tolerance of the arithmetic progression and equal to the difference between the arrangement interval between the first processed part and the second processed part and the tolerance.

In addition, it is preferable that the needle tip part position estimation unit displays the estimated position of the needle tip part on the display unit.

The ultrasound diagnostic apparatus may further comprise an ultrasound probe and an image acquisition unit that acquires the ultrasound image by performing transmission and reception of an ultrasound beam between the ultrasound probe and a subject. In this case, the display unit may display the ultrasound image acquired by the image acquisition unit, and the arrangement interval detection unit may recognize the plurality of processed parts of the puncture needle and detect the arrangement intervals of the plurality of processed parts by image analysis of the ultrasound image acquired by the image acquisition unit.

A control method of an ultrasound diagnostic apparatus according to a third aspect of the present invention comprises displaying an ultrasound image in which the puncture needle is captured, recognizing the plurality of processed parts of the puncture needle and detecting the arrangement intervals of the plurality of processed parts by image analysis of the ultrasound image, determining whether or not the detected arrangement intervals of the plurality of processed parts form the arithmetic progression, calculating the tolerance of the arithmetic progression and detecting the first processed part which is closest to the needle tip part among the plurality of processed parts based on the tolerance in a case where determination is made that the arithmetic progression is formed, and estimating a position of the needle tip part based on a position of the detected first processed part.

According to the present invention, a puncture needle comprises a shaft part, a needle tip part disposed at a tip of the shaft part, and a plurality of processed parts that are arranged on an outer peripheral part of the shaft part along a length direction of the shaft part and form an arithmetic progression in which arrangement intervals gradually decrease toward the needle tip part, in which among the plurality of processed parts, an arrangement interval between a first processed part which is separated from the needle tip part by a predetermined distance and is closest to the needle tip part and a second processed part which is second closest to the needle tip part is equal to or less than a tolerance of the arithmetic progression, or a distance from the needle tip part to the first processed part which is closest to the needle tip part is equal to or less than the tolerance of the arithmetic progression and equal to a difference between the arrangement interval between the first processed part and the second processed part which is second closest to the needle tip part and the tolerance. Therefore, a user can accurately grasp the tip part of the puncture needle.

DESCRIPTION OF THE PREFERRED EMBODIMENTS

Hereinafter, embodiments of the present invention will be described with reference to the accompanying drawings.

Description of constituents described below may be made based on a typical embodiment of the present invention, but the present invention is not limited to such an embodiment.

Embodiment 1

Figure 1:
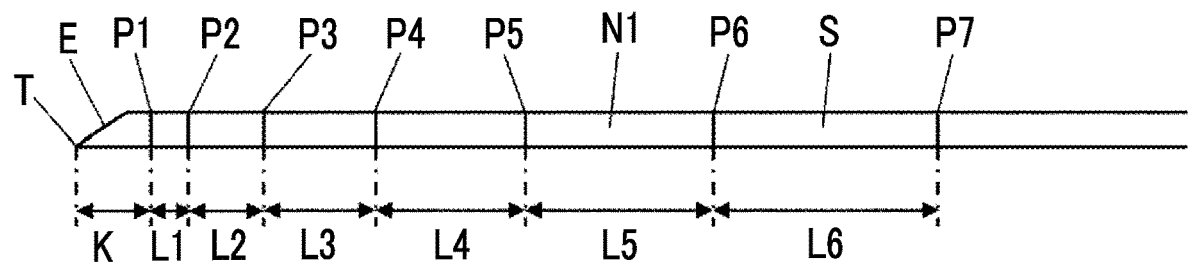
FIG. 1 is a diagram showing a puncture needle according to Embodiment 1 of the present invention.

FIG. 1 shows a puncture needle N1 according to Embodiment 1 of the present invention. The puncture needle N1 is inserted into a subject in order to place a catheter, a drug, or the like in the subject, and comprises a shaft part S and a sharp needle tip part T formed by obliquely cutting out a tip part of the shaft part S and disposed at a tip of the shaft part S. In the shaft part S, a plurality of processed parts P1 to P7 formed of grooves formed to surround a periphery of the shaft part S are arranged and formed along a length direction of the shaft part S. In addition, an arrangement interval L1 between the first processed part P1 and the second processed part P2, an arrangement interval L2 between the second processed part P2 and the third processed part P3, an arrangement interval L3 between the third processed part P3 and the fourth processed part P4, an arrangement interval L4 between the fourth processed part P4 and the fifth processed part P5, an arrangement interval L5 between the fifth processed part P5 and the sixth processed part P6, and an arrangement interval L6 between the sixth processed part P6 and the seventh processed part P7 form an arithmetic progression in which values gradually decrease toward the needle tip part T. Here, the term "the arrangement intervals form the arithmetic progression" means that values of the arrangement intervals form the arithmetic progression, and that in a case where values of the arrangement intervals L1 to L6 are integers and are aligned to a specific unit such as mm, the values form the arithmetic progression. Therefore, in the arrangement intervals L1 to L6 of the plurality of processed parts P1 to P7, a difference between arrangement intervals adjacent to each other is a so-called tolerance of the arithmetic progression and each has the same value.

Among the plurality of processed parts P1 to P7, the arrangement interval L1 between the first processed part P1 which is separated from the needle tip part T by a predetermined distance K and is closest to the needle tip part T and the second processed part P2 which is second closest to the needle tip part T is designed to be equal to or less than the tolerance of the arithmetic progression formed by the arrangement intervals of the plurality of processed parts P1 to P7. For example, assuming that the arrangement interval L1 between the first processed part P1 and the second processed part P2 is 5 mm, the arrangement interval L2 between the second processed part P2 and the third processed part P3 is 10 mm, the arrangement interval L3 between the third processed part P3 and the fourth processed part P4 is 15 mm, the arrangement interval L4 between the fourth processed part P4 and the fifth processed part P5 is 20 mm, the arrangement interval L5 between the fifth processed part P5 and the sixth processed part P6 is 25 mm, and the arrangement interval L6 between the sixth processed part P6 and the seventh processed part P7 is 30 mm, the first processed part P1 to the seventh processed part P7 can form an arithmetic progression with a tolerance of 5 mm, and the first processed part P1 to the seventh processed part P7 can be formed such that the arrangement interval L1 between the first processed part P1 and the second processed part P2 is equal to the tolerance of 5 mm.

In addition, as shown in FIG. 1, since the needle tip part T is formed by obliquely cutting out the tip part of the shaft part S, an inclined surface E inclined by a predetermined inclination angle with respect to an extending direction of the shaft part S is formed at a tip part of the shaft part S, and the first processed part P1 is formed on a base end side of the shaft part S from the inclined surface E. Therefore, a formation position of the first processed part P1 can be appropriately set according to the specifications of the puncture needle N1, such as an outer diameter of the shaft part S and the inclination angle of the inclined surface E with respect to the extending direction of the shaft part S.

Figure 2:
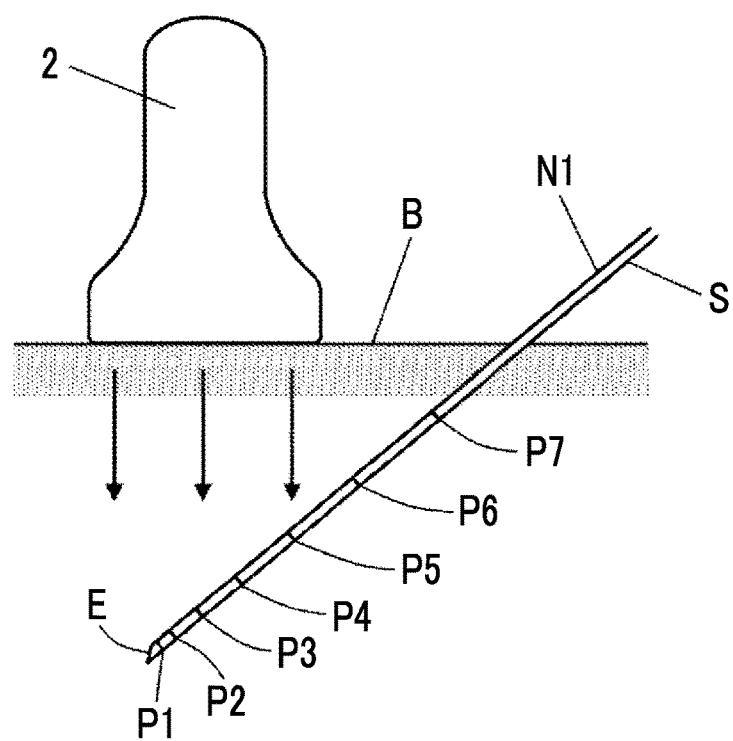
FIG. 2 is a diagram schematically showing a state where the puncture needle according to Embodiment 1 of the present invention is inserted into a subject and the puncture needle is irradiated with an ultrasound beam.

As shown in FIG. 2, the puncture needle N1 according to Embodiment 1 of the present invention as described above is irradiated with an ultrasound beam from an ultrasound probe 2 in contact with a body surface B of the subject while being inserted into the subject. The ultrasound beam applied to the puncture needle is reflected by the plurality of processed parts P1 to P7, and the reflected ultrasound beam propagates toward the ultrasound probe 2. Thus, in a case where the puncture needle N1 is imaged by the ultrasound probe 2, a plurality of processed parts P1 to P7 of the puncture needle N1 are depicted in an ultrasound image.

Here, in the puncture needle N1 according to Embodiment 1 of the present invention, since the first processed part P1 is formed on the base end side of the shaft part S from the inclined surface E, the first processed part P1 can be depicted in the ultrasound image regardless of a rotation angle around a central axis of the puncture needle N1.

Figure 3:
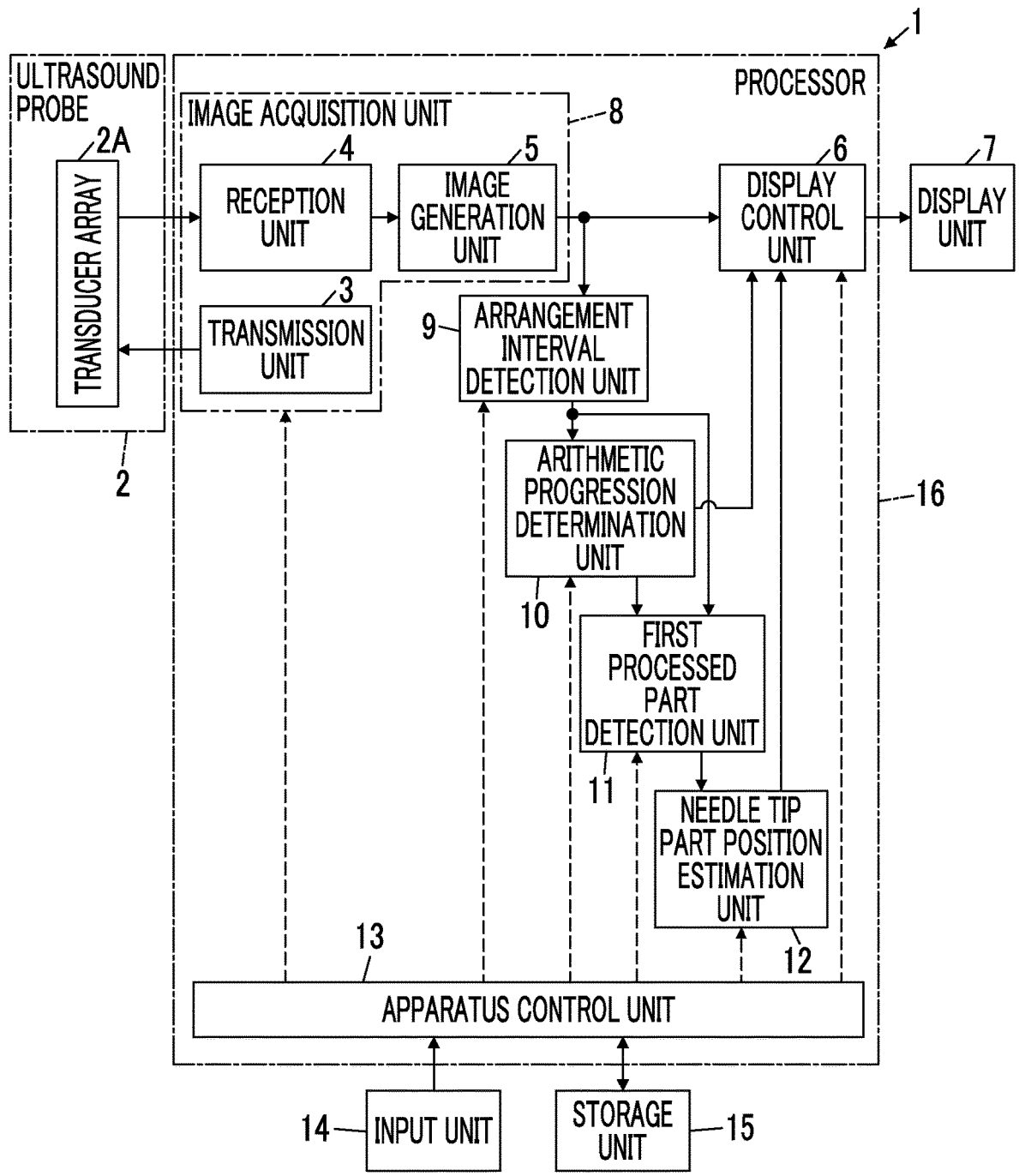
FIG. 3 is a block diagram showing a configuration of an ultrasound diagnostic apparatus according to Embodiment 1 of the present invention.

Next, an ultrasound diagnostic apparatus 1 according to Embodiment 1 of the present invention will be described. The ultrasound diagnostic apparatus 1 images the puncture needle N1 inserted into the subject. As shown in FIG. 3, the ultrasound diagnostic apparatus 1 comprises the ultrasound probe 2 incorporating a transducer array 2A, and a transmission unit 3 and a reception unit 4 are connected to the transducer array 2A. An image generation unit 5, a display control unit 6, and a display unit 7 are sequentially connected to the reception unit 4. Here, an image acquisition unit 8 is constituted of the transmission unit 3, the reception unit 4, and the image generation unit 5. In addition, an arrangement interval detection unit 9 is connected to the image generation unit 5, and an arithmetic progression determination unit 10 and a first processed part detection unit 11 are connected to the arrangement interval detection unit 9. The display control unit 6 and the first processed part detection unit 11 are connected to the arithmetic progression determination unit 10. A needle tip part position estimation unit 12 is connected to the first processed part detection unit 11, and the display control unit 6 is connected to the needle tip part position estimation unit 12.

Further, an apparatus control unit 13 is connected to the display control unit 6, the image acquisition unit 8, the arrangement interval detection unit 9, the arithmetic progression determination unit 10, the first processed part detection unit 11, and the needle tip part position estimation unit 12, and an input unit 14 and a storage unit 15 are connected to the apparatus control unit 13. Here, the apparatus control unit 13 and the storage unit 15 are connected to each other so that information can be exchanged in both directions.

In addition, a processor 16 is constituted of the display control unit 6, the image acquisition unit 8, the arrangement interval detection unit 9, the arithmetic progression determination unit 10, the first processed part detection unit 11, the needle tip part position estimation unit 12, and the apparatus control unit 13.

The transducer array 2A of the ultrasound probe 2 shown in FIG. 3 has a plurality of transducers arranged one-dimensionally or two-dimensionally. Each of these transducers transmits an ultrasonic wave in accordance with a drive signal supplied from the transmission unit 3, and receives an ultrasound echo from the subject to output a reception signal. Each transducer is constituted by forming electrodes on both ends of a piezoelectric body made of, for example, a piezoelectric ceramic represented by lead zirconate titanate (PZT), a polymer piezoelectric element represented by poly vinylidene di fluoride (PMN-PT: polyvinylidene fluoride), and a piezoelectric single crystal represented by lead magnesium niobate-lead titanate (PMN-PT: lead magnesium niobate-lead titanate solid solution).

The transmission unit 3 of the image acquisition unit 8 includes, for example, a plurality of pulse generators, and based on a transmission delay pattern selected in accordance with a control signal from the apparatus control unit 13, supplies the drive signals to the plurality of transducers by adjusting the delay amount so that the ultrasonic waves transmitted from the plurality of transducers of the transducer array 2A form an ultrasound beam. In this way, in a case where a pulsed or continuous wave voltage is applied to the electrodes of the plurality of transducers of the transducer array 2A, the piezoelectric body expands and contracts, pulsed or continuous wave ultrasonic waves are generated from the transducers, and an ultrasound beam is formed from a composite wave of the ultrasonic waves.

The transmitted ultrasound beam is reflected at an object such as a part of the subject and propagates toward the transducer array 2A of the ultrasound probe 2. The ultrasound echo propagating toward the transducer array 2A in this way is received by each of the transducers constituting the transducer array 2A. In this case, each transducer constituting the transducer array 2A expands and contracts by receiving the propagating ultrasound echo to generate an electric signal, and outputs these electric signals to the reception unit 4.

Figure 4:
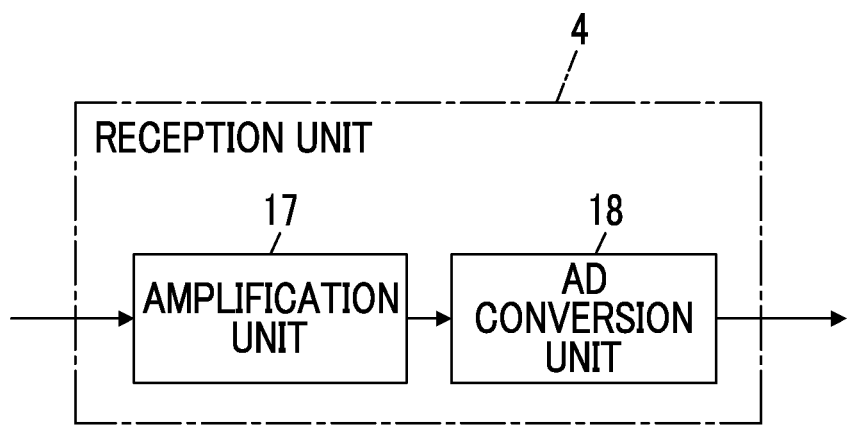
FIG. 4 is a block diagram showing a configuration of a reception unit in Embodiment 1 of the present invention.

The reception unit 4 of the image acquisition unit 8 processes a signal output from the transducer array 2A in accordance with the control signal from the apparatus control unit 13. As shown in FIG. 4, the reception unit 4 has a configuration in which an amplification unit 17 and an analog digital (AD) conversion unit 18 are connected in series. The amplification unit 17 amplifies the signal received from each of the transducers constituting the transducer array 2A, and transmits the amplified signal to the AD conversion unit 18. The AD conversion unit 18 converts the signal transmitted from the amplification unit 17 into a digitized reception signal, and sends these pieces of data to the image generation unit 5 of the image acquisition unit 8.

Figure 5:
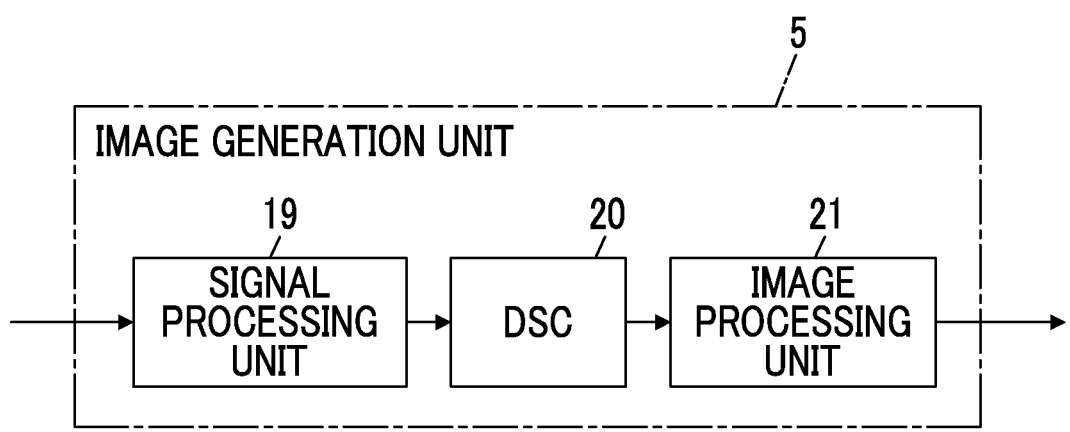
FIG. 5 is a block diagram showing a configuration of an image generation unit in Embodiment 1 of the present invention.

As shown in FIG. 5, the image generation unit 5 of the image acquisition unit 8 has a configuration in which a signal processing unit 19, a digital scan converter (DSC) 20, and an image processing unit 21 are sequentially connected in series. The signal processing unit 19 performs reception focus processing by applying a delay to each piece of data of the reception signal based on a reception delay pattern selected in accordance with the control signal from the apparatus control unit 13, and adding up the results (phase-adjusted addition). By the reception focus processing, a sound ray signal in which a focus of the ultrasound echo is narrowed down to one scanning line is generated. In addition, the signal processing unit 19 corrects attenuation caused by a propagation distance of the generated sound ray signal according to a depth of a position where the ultrasonic wave is reflected, and then performs envelope detection processing to generate a B-mode image signal representing a tissue in the subject. The B-mode image signal generated in this way is output to the DSC 20.

The DSC 20 of the image generation unit 5 generates an ultrasound image by raster-converting the B-mode image signal into an image signal according to a normal television signal scanning method. The image processing unit 21 of the image generation unit 5 performs various kinds of necessary image processing such as brightness correction, gradation correction, sharpness correction, and color correction on the ultrasound image obtained by the DSC 20, and then outputs the ultrasound image to the display control unit 6 and the arrangement interval detection unit 9.

The arrangement interval detection unit 9 of the processor 16 recognizes the plurality of processed parts P1 to P7 of the puncture needle N1 and detects arrangement intervals of the plurality of processed parts P1 to P7 by image analysis of the ultrasound image in which the puncture needle N1 is captured.

The arithmetic progression determination unit 10 of the processor 16 determines whether or not the arrangement intervals of the plurality of processed parts P1 to P7 detected by the arrangement interval detection unit 9 form the arithmetic progression. The arithmetic progression determination unit 10 can determine whether or not the arrangement intervals of the plurality of processed parts P1 to P7 form the arithmetic progression, for example, by determining whether or not a plurality of the arrangement intervals detected by the arrangement interval detection unit 9 gradually decrease by a certain length in one direction along an arrangement direction of the plurality of processed parts P1 to P7. Even in a case where the actually detected values are, for example, 4.9 mm for the arrangement interval L1, 10.1 mm for the arrangement interval L2, and 14.9 mm for the arrangement interval L3, determination may be made whether or not the arithmetic progression is formed by approximating the values to integer values.

The first processed part detection unit 11 of the processor 16 detects the first processed part P1 closest to the needle tip part T among the plurality of processed parts P1 to P7 of the puncture needle N1 by using the plurality of arrangement intervals detected by the arrangement interval detection unit 9 based on a determination result by the arithmetic progression determination unit 10. In this case, in a case where the arithmetic progression determination unit 10 determines that the arithmetic progression is formed, the first processed part detection unit 11 calculates the tolerance of the arithmetic progression and detects the first processed part P1 based on the calculated tolerance.

Here, for example, any one of the plurality of processed parts P1 to P7 of the puncture needle N1 may be concealed or disappear in the ultrasound image due to a high-intensity reflection signal, a so-called acoustic shadow, or the like derived from the tissue in the subject. In this case, the arithmetic progression determination unit 10 determines that the arithmetic progression is not formed, but in this case, the first processed part detection unit 11 estimates the processed part concealed or disappearing due to the high-intensity reflection signal, the acoustic shadow, or the like based on the plurality of arrangement intervals detected by the arrangement interval detection unit 9, to calculate the tolerance of the arithmetic progression formed by the arrangement intervals of the plurality of processed parts P1 to P7, and detects the first processed part P1 based on the calculated tolerance.

The needle tip part position estimation unit 12 of the processor 16 estimates a position of the needle tip part T based on the position of the first processed part P1 detected by the first processed part detection unit 11, and displays the estimated position of the needle tip part T on the display unit 7. For example, the needle tip part position estimation unit 12 estimates, as the position of the needle tip part, a point extending from the first processed part P1 to a tip side of the shaft part S by a predetermined distance K along the length direction of the shaft part S, in a case where the arrangement interval L1 between the first processed part P1 and the second processed part P2 of the puncture needle N1, the interval being detected by the arrangement interval detection unit 9, is equal to or less than the tolerance calculated by the first processed part detection unit 11.

Here, the needle tip part position estimation unit 12 may use, for example, a value stored in advance as the predetermined distance K, or may use a value input by the user via the input unit 14.

The apparatus control unit 13 of the processor 16 controls each unit of the ultrasound diagnostic apparatus 1 based on a program recorded in advance in the storage unit 15 or the like and an input operation by the user via the input unit 14.

The display control unit 6 of the processor 16, under the control of the apparatus control unit 13, causes the display unit 7 to display the ultrasound image generated by the image generation unit 5 of the image acquisition unit 8, the position of the needle tip part T estimated by the needle tip part position estimation unit 12, and the like.

The display unit 7 of the ultrasound diagnostic apparatus 1 displays the ultrasound image generated by the image acquisition unit 8, the position of the needle tip part T estimated by the needle tip part position estimation unit 12, and the like, and includes, for example, a display device such as a liquid crystal display (LCD) or an organic EL display (organic electroluminescence display).

The input unit 14 of the ultrasound diagnostic apparatus 1 is for the user to perform an input operation, and may comprise a keyboard, a mouse, a trackball, a touch pad, a touch panel, and the like.

The storage unit 15 stores an operation program or the like of the ultrasound diagnostic apparatus 1, and may use a recording medium such as a flash memory, a hard disc drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), and a universal serial bus memory (USB memory), or a server.

The processor 16 having the display control unit 6, the image acquisition unit 8, the arrangement interval detection unit 9, the arithmetic progression determination unit 10, the first processed part detection unit 11, the needle tip part position estimation unit 12, and the apparatus control unit 13 is constituted of a central processing unit (CPU) and a control program for causing the CPU to perform various kinds of processing, and may be constituted of a field programmable gate array (FPGA), a digital signal processor (DSP), an application specific integrated circuit (ASIC), a graphics processing unit (GPU), or other integrated circuit (IC) or a combination thereof.

The display control unit 6, the image acquisition unit 8, the arrangement interval detection unit 9, the arithmetic progression determination unit 10, the first processed part detection unit 11, the needle tip part position estimation unit 12, and the apparatus control unit 13 of the processor 16 may be partially or entirely integrated into one CPU or the like.

Figure 6:
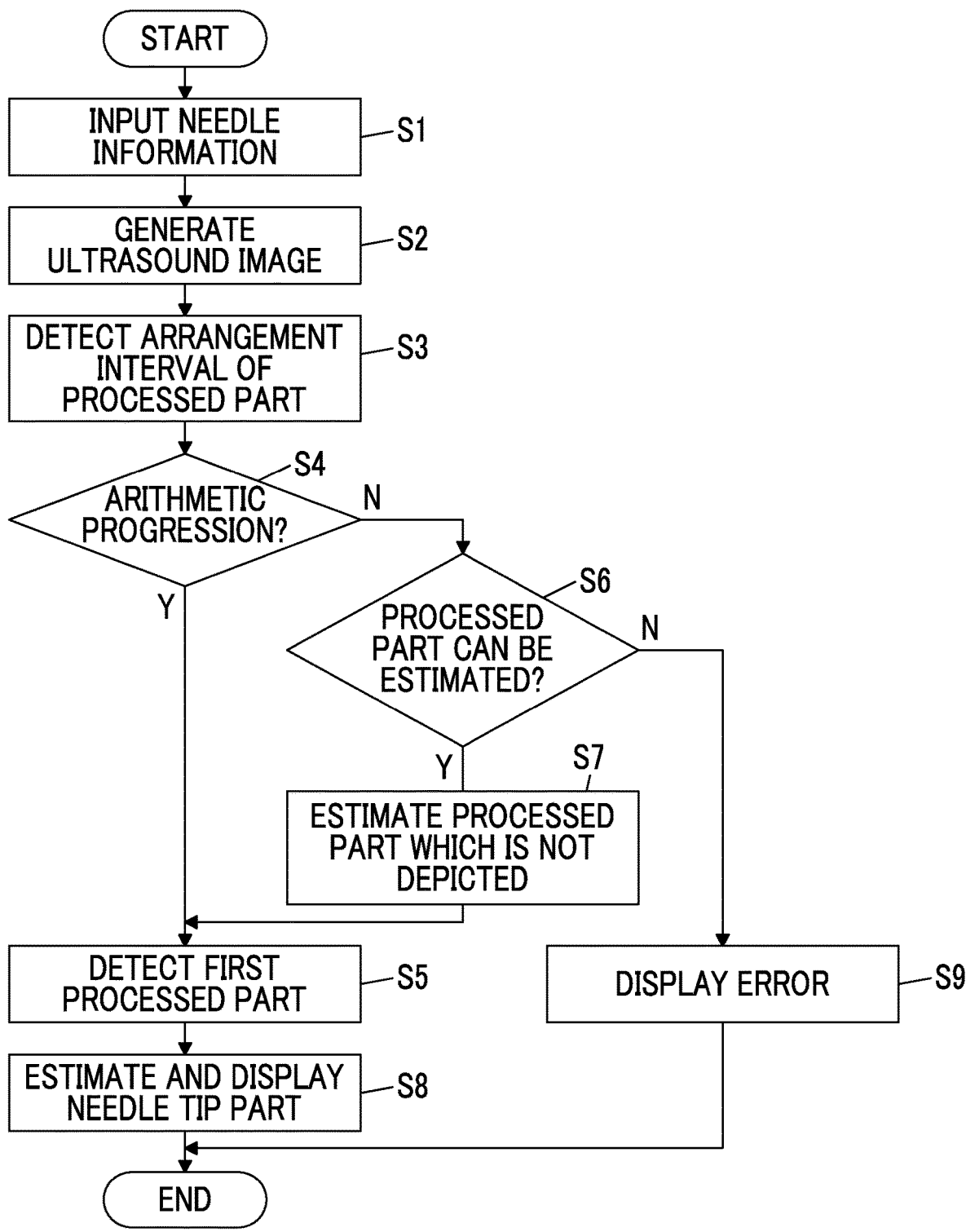
FIG. 6 is a flowchart showing an operation of the ultrasound diagnostic apparatus in Embodiment 1 of the present invention.

Next, the operation of the ultrasound diagnostic apparatus 1 in Embodiment 1 will be described in detail with reference to the flowchart shown in FIG. 6.

First, in step S1, needle information, which is information of the puncture needle N1, is input by the user via the input unit 14. The needle information input here includes the predetermined distance K from the needle tip part T to the first processed part P1.

In the following step S2, as shown in FIG. 2, an ultrasound beam is applied from the ultrasound probe 2 in contact with the body surface B of the subject toward the puncture needle N1 in the subject, and an ultrasound image is captured. In this case, ultrasound echoes from the subject and the puncture needle N1 are received by the transducer array 2A of the ultrasound probe 2 to generate a reception signal, and the generated reception signal is amplified by the amplification unit 17 of the reception unit 4, and A/D conversion is performed by the A/D conversion unit 18. Further, the reception signal subjected to the A/D conversion is output to the image generation unit 5, and the image generation unit 5 generates an ultrasound image based on the reception signal.

In step S3, the arrangement interval detection unit 9 recognizes the plurality of processed parts P1 to P7 of the puncture needle N1 and detects the arrangement intervals of the plurality of processed parts P1 to P7 by image analysis of the ultrasound image generated in step S2.

In step S4, the arithmetic progression determination unit 10 determines whether or not the plurality of arrangement intervals detected in step S3 form an arithmetic progression. In a case where determination is made in step S4 that the plurality of arrangement intervals form an arithmetic progression, the process proceeds to step S5.

In step S5, the first processed part detection unit 11 calculates the tolerance of the arithmetic progression from the plurality of arrangement intervals detected in step S3, and specifies an arrangement interval equal to or less than the calculated tolerance as the arrangement interval L1 between the first processed part P1 and the second processed part P2 to detect the first processed part P1.

Here, since the plurality of arrangement intervals detected in step S3 are arranged so as to form the arithmetic progression along the arrangement direction of the plurality of processed parts P1 to P7 depicted in the ultrasound image, a length obtained by subtracting the tolerance from the arrangement interval on the base end side of the puncture needle N1 is equal to a length of the arrangement interval adjacent to the needle tip part T side of the puncture needle N1. Therefore, in a case where an arrangement interval having a length equal to or less than the tolerance is detected, there is no arrangement interval adjacent to the needle tip part T side of the puncture needle N1 from the detected arrangement interval, and it is understood that the arrangement interval having a length equal to or less than the tolerance is the arrangement interval L1 between the first processed part P1 closest to the needle tip part T and the second processed part P2 which is second closest to the needle tip part T. That is, the first processed part detection unit 11 can detect the first processed part P1 by specifying the arrangement interval equal to or less than the tolerance as the arrangement interval L1.

In a case where the arithmetic progression determination unit 10 determines in step S4 that the arithmetic progression is not formed, the process proceeds to step S6.

Here, for example, due to a high-intensity reflection signal, a so-called acoustic shadow, or the like derived from the tissue in the subject, a part of the plurality of processed parts P1 to P7 of the puncture needle N1 may not be depicted, such as any one of the plurality of processed parts P1 to P7 being concealed or disappearing in the ultrasound image. In a case where the puncture needle N1 according to Embodiment 1 of the present invention is inserted into the subject, even though a part of the plurality of processed parts P1 to P7 of the puncture needle N1 is not depicted in the ultrasound image, it may be possible to estimate the processed part which is not depicted.

Figure 7:
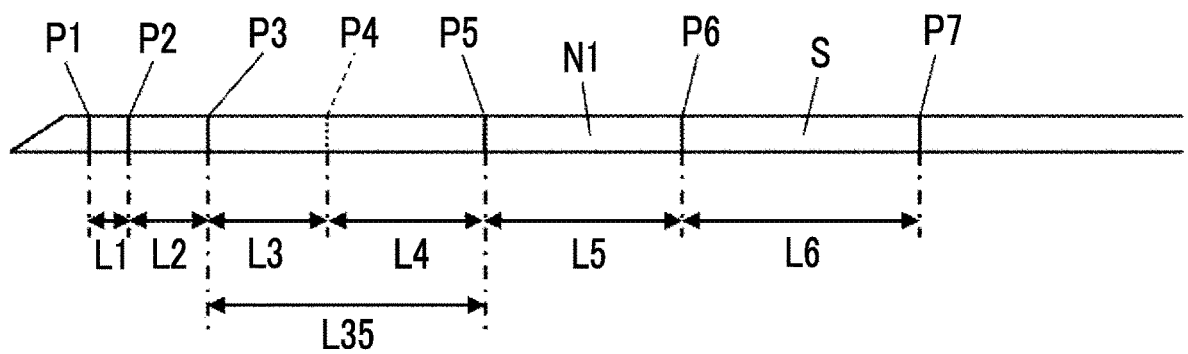
FIG. 7 is a diagram schematically showing a state where one processed part is not depicted in an ultrasound image in Embodiment 1 of the present invention.

For example, as shown in FIG. 7, in a case where the fourth processed part P4 among the plurality of processed parts P1 to P7 is not depicted in the ultrasound image, the arrangement interval L1 between the first processed part P1 and the second processed part P2, the arrangement interval L2 between the second processed part P2 and the third processed part P3, an arrangement interval L35 between the third processed part P3 and the fifth processed part P5, the arrangement interval L5 between the fifth processed part P5 and the sixth processed part P6, and the arrangement interval L6 between the sixth processed part P6 and the seventh processed part P7 are detected in step S3. In this case, a tolerance can be calculated by a difference between the arrangement interval L1 and the arrangement interval L2 among the three consecutive processed parts P1, P2, and P3 and a difference between the arrangement interval L5 and the arrangement interval L6 among the three consecutive processed parts P5, P6, and P7. Further, according to the calculated tolerance, it is estimated that the arrangement interval L35 between the third processed part P3 and the fifth processed part P5 is a sum of the arrangement interval L3 between the third processed part P3 and the fourth processed part P4 and the arrangement interval L4 between the fourth processed part P4 and the fifth processed part P5. Finally, it is confirmed that the estimated arrangement intervals L3 and L4 and the arrangement intervals L1, L2, L5, and L6 estimated in step S3 form an arithmetic progression, and thus, the processed part P4 which is not depicted in the ultrasound image can be estimated with high accuracy.

Figure 8:
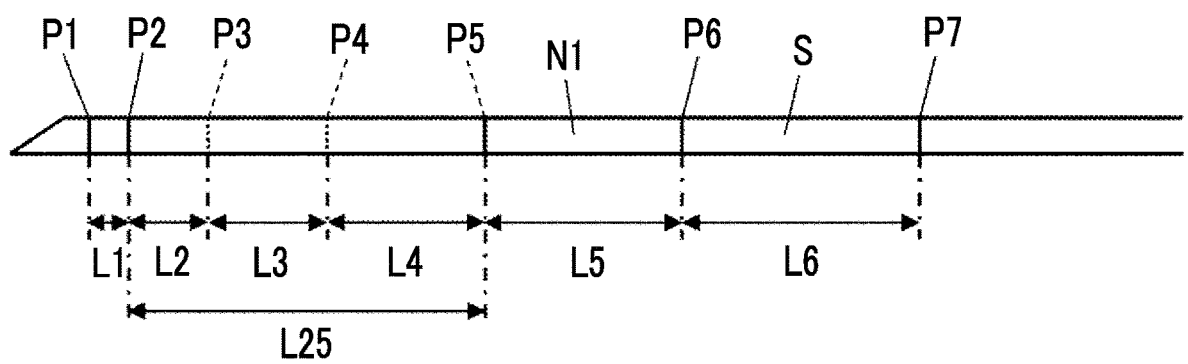
FIG. 8 is a diagram schematically showing a state where two processed parts are not depicted in the ultrasound image in Embodiment 1 of the present invention.

In addition, for example, as shown in FIG. 8, in a case where the third processed part P3 and the fourth processed part P4 among the plurality of processed parts P1 to P7 are not depicted in the ultrasound image, the arrangement interval L1 between the first processed part P1 and the second processed part P2, an arrangement interval L25 between the second processed part P2 and the fifth processed part P5, the arrangement interval L5 between the fifth processed part P5 and the sixth processed part P6, and the arrangement interval L6 between the sixth processed part P6 and the seventh processed part P7 are detected in step S3. In this case, since the arrangement interval L5 and the arrangement interval L6 among the three consecutive processed parts P5, P6, and P7 are detected in step S3, a tolerance can be calculated by a difference between the arrangement interval L5 and the arrangement interval L6. Further, according to the calculated tolerance, it is estimated that the arrangement interval L25 between the second processed part P2 and the fifth processed part P5 is a sum of the arrangement interval L2 between the second processed part P2 and the third processed part P3, the arrangement interval L3 between the third processed part P3 and the fourth processed part P4, and the arrangement interval L4 between the fourth processed part P4 and the fifth processed part P5. Finally, it is confirmed that the estimated arrangement intervals L2, L3, and L4 and the arrangement intervals L1, L5, and L6 estimated in step S3 form an arithmetic progression, and thus, the third processed part P3 and the fourth processed part P4 which are not depicted in the ultrasound image can be estimated with high accuracy.

Therefore, in step S6, the arithmetic progression determination unit 10 determines whether or not the processed part which is not depicted in the ultrasound image can be estimated. In a case where determination is made in step S6 that the processed part which is not depicted in the ultrasound image can be estimated, the process proceeds to step S7.

In step S7, the first processed part detection unit 11 calculates the tolerance of the arithmetic progression from the plurality of arrangement intervals detected in step S3, and estimates the processed part which is not depicted in the ultrasound image using the calculated tolerance. In this way, in a case where the processed part which is not depicted in the ultrasound image is estimated, the process proceeds to step S5.

In step S5, the first processed part detection unit 11 detects the first processed part P1 by specifying an arrangement interval equal to less than the tolerance calculated in step S7 as the arrangement interval L1 between the first processed part P1 and the second processed part P2 among the arrangement intervals of the plurality of processed parts P1 to P7 while taking into consideration a position of the processed part estimated in step S7. In this way, in a case where the first processed part P1 is detected, the process proceeds to step S8.

Figure 9:
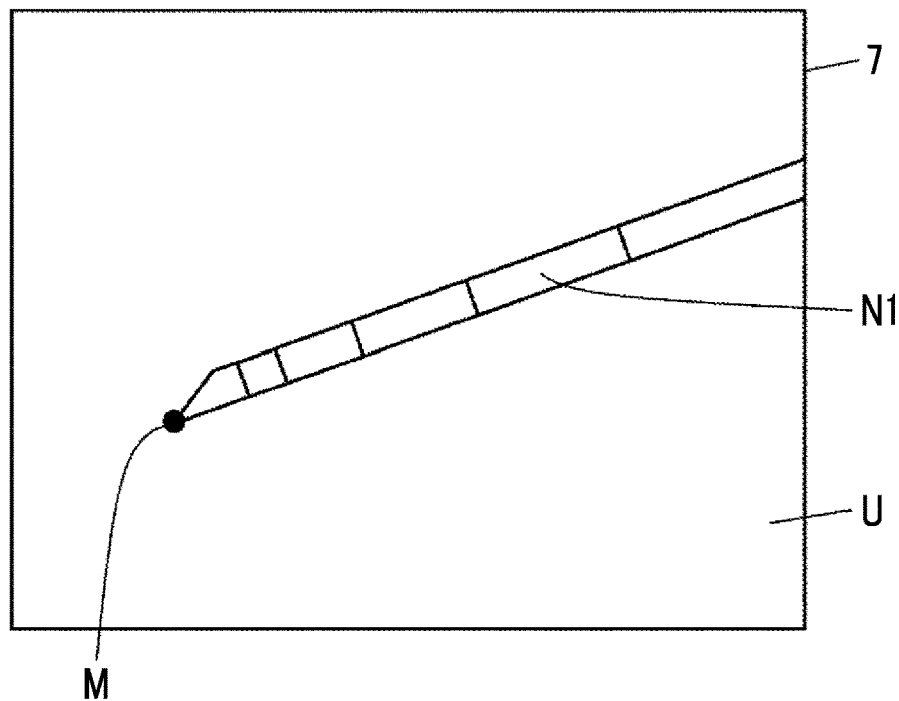
FIG. 9 is a diagram schematically showing a state where a position of a needle tip part is displayed on the ultrasound image in Embodiment 1 of the present invention.

In step S8, the needle tip part position estimation unit 12 estimates, as a position of the needle tip part T, a point extending from the first processed part P1 detected in step S5 to a tip side of the shaft part S by a predetermined distance K along the arrangement direction of the plurality of processed parts P1 to P7, that is, the length direction of the shaft part S of the puncture needle N1. Further, the needle tip part position estimation unit 12 superimposes the estimated position of the needle tip part T on the ultrasound image generated in step S2 and causes the display unit 7 to display the image. For example, as shown in FIG. 9, the needle tip part position estimation unit 12 superimposes a tip mark M representing the position of the needle tip part T of the puncture needle N1 on an ultrasound image U and displays the image on the display unit 7. In the example shown in FIG. 9, the tip mark M is indicated by a black circle for description.

In a case where the process of step S8 is completed in this way, the operation of the ultrasound diagnostic apparatus 1 ends.

In addition, in step S6, in a case where the arithmetic progression determination unit 10 determines that the plurality of arrangement intervals detected in step S3 are not allowed to form an arithmetic progression and that a processed part which is not depicted in the ultrasound image U cannot be estimated, the process proceeds to step S9. Here, for example, in a case where three consecutive processed parts among the plurality of processed parts P1 to P7 are not depicted in the ultrasound image U and a tolerance cannot be calculated, or in a case where a puncture needle having no processed parts arranged in accordance with an arithmetic progression is inserted into the subject, instead of the puncture needle N1 according to Embodiment 1 of the present invention, the plurality of arrangement intervals detected in step S3 are not allowed to form an arithmetic progression.

In step S9, the arithmetic progression determination unit 10 displays, although not shown, occurrence of an error on the display unit 7. In this way, in a case where the process of step S9 is completed, the operation of the ultrasound diagnostic apparatus 1 ends.

As described above, the puncture needle N1 according to Embodiment 1 of the present invention comprises the plurality of processed parts P1 to P7 forming an arithmetic progression in which values gradually decrease toward the needle tip part T, a distance between the needle tip part T and the first processed part P1 is a predetermined distance K, and the arrangement interval between the first processed part P1 and the second processed part P2 is equal to or less than the tolerance of the arithmetic progression. Therefore, for example, the ultrasound diagnostic apparatus 1 easily estimates the position of the needle tip part T and displays the estimated position of the needle tip part T on the display unit 7. Thus, the user can accurately grasp the position of the needle tip part T of the puncture needle N1 by confirming the display unit 7.

According to the ultrasound diagnostic apparatus 1 according to Embodiment 1 of the present invention, since the plurality of processed parts P1 to P7 are recognized to detect the arrangement intervals of the plurality of processed parts P1 to P7 by image analysis of the ultrasound image U, whether or not the detected plurality of arrangement intervals form an arithmetic progression is determined, a tolerance of the arithmetic progression is calculated, the first processed part P1 is detected based on the calculated tolerance, and the position of the needle tip part T is estimated based on the position of the detected first processed part P1, the position of the needle tip part T can be estimated with high accuracy.

Further, according to the ultrasound diagnostic apparatus 1 according to Embodiment 1 of the present invention, even in a case where any one of the plurality of processed parts P1 to P7 of the puncture needle N1 is concealed or disappears in the ultrasound image U due to a high-intensity reflection signal, an acoustic shadow, or the like derived from the tissue in the subject, the first processed part detection unit 11 estimates a position of the concealed or disappearing processed part. Therefore, the position of the needle tip part T can be estimated with high accuracy.

In the example shown in FIG. 1, although seven processed parts P1 to P7 are formed in the shaft part S from the needle tip part T of the puncture needle N1 toward a base end part of the shaft part S, the number of processed parts is not limited to seven. The number of processed parts formed in the shaft part S may be more than seven, and for example, a plurality of processed parts (not shown) forming an arithmetic progression together with the processed parts P1 to P7 may be provided on the base end part side from the processed part P7. In addition, the number of processed parts may be less than seven, and may be, for example, six or five.

In Embodiment 1, although the first processed part P1 is formed at a position separated from the needle tip part T of the puncture needle N1 by the predetermined distance K, a length of the predetermined distance K is not particularly limited. However, the shorter the predetermined distance K, that is, the closer the first processed part P1 is formed to the needle tip part T, the less likely it is to be affected by deflection of the puncture needle N1 or the like in a case where the position of the needle tip part T is estimated based on the position of the first processed part P1. Therefore, estimation accuracy of the needle tip part T can be improved. Therefore, from the viewpoint of improving the estimation accuracy of the needle tip part T, the length of the predetermined distance K is preferably shorter, for example, the arrangement interval L1 between the first processed part P1 and the second processed part P2 or less.

Although not shown, the ultrasound diagnostic apparatus 1 comprises a needle information acquisition unit that acquires needle information of the puncture needle N1 by scanning the puncture needle N1, reading a bar code attached to a packaging bag of the puncture needle N1, or the like. Thus, for example, the user can save time and effort of manually inputting the needle information via the input unit 14.

Embodiment 2

In the puncture needle N1 of Embodiment 1, the arithmetic progression is formed by the arrangement intervals of the plurality of processed parts P1 to P7, but the arithmetic progression may be formed by the distance from the needle tip part to the first processed part P1 and the arrangement intervals of the plurality of processed parts P1 to P7.

Figure 10:
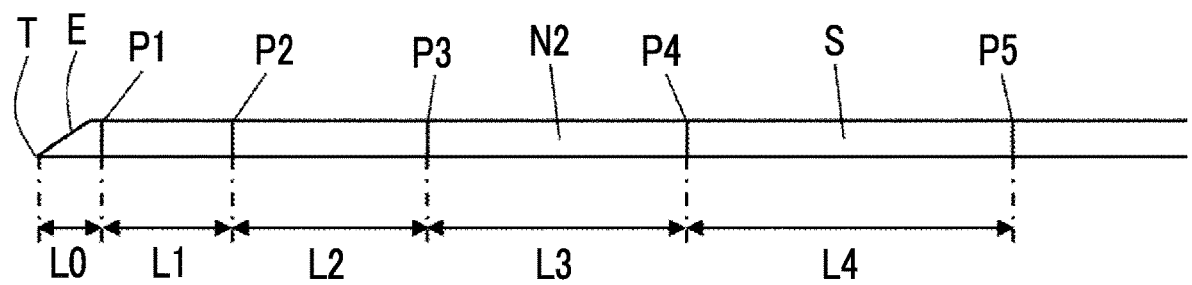
FIG. 10 is a diagram showing a puncture needle according to Embodiment 2 of the present invention.

As shown in FIG. 10, although a puncture needle N2 according to Embodiment 2 of the present invention, similarly to the puncture needle N1 of Embodiment 1 shown in FIG. 1, comprises a shaft part S and a needle tip part T disposed at a tip of the shaft part S, and a plurality of processed parts P1 to P5 are arranged and formed on the shaft part S, a distance L0 from the needle tip part T to the first processed part P1 and arrangement intervals L1 to L4 of the plurality of processed parts P1 to P5 form an arithmetic progression in which values gradually decrease toward the needle tip part T. Therefore, a difference between the distance L0 from the needle tip part T to the first processed part P1 and the arrangement interval L1 between the first processed part P1 and the second processed part P2 and a difference between arrangement intervals adjacent to each other in the arrangement intervals L1 to L4 are a tolerance of the arithmetic progression and each have the same value.

Here, it is assumed that the distance L0 from the needle tip part T to the first processed part P1 is set so as to be equal to or less than the tolerance of the arithmetic progression and equal to a difference between the arrangement interval L1 between the first processed part P1 and the second processed part P2 and the tolerance of the arithmetic progression. In this way, since the distance L0 from the needle tip part T to the first processed part P1 and the arrangement intervals L1 to L4 of the plurality of processed parts P1 to P5 form an arithmetic progression in which values gradually decrease toward the needle tip part T, and the distance L0 from the needle tip part T to the first processed part P1 is equal to or less than the tolerance of the arithmetic progression, a position of the needle tip part T can be estimated by acquiring the tolerance of the arithmetic progression, the arrangement interval L1 between the first processed part P1 and the second processed part P2, and the position of the first processed part P1.

Figure 11:
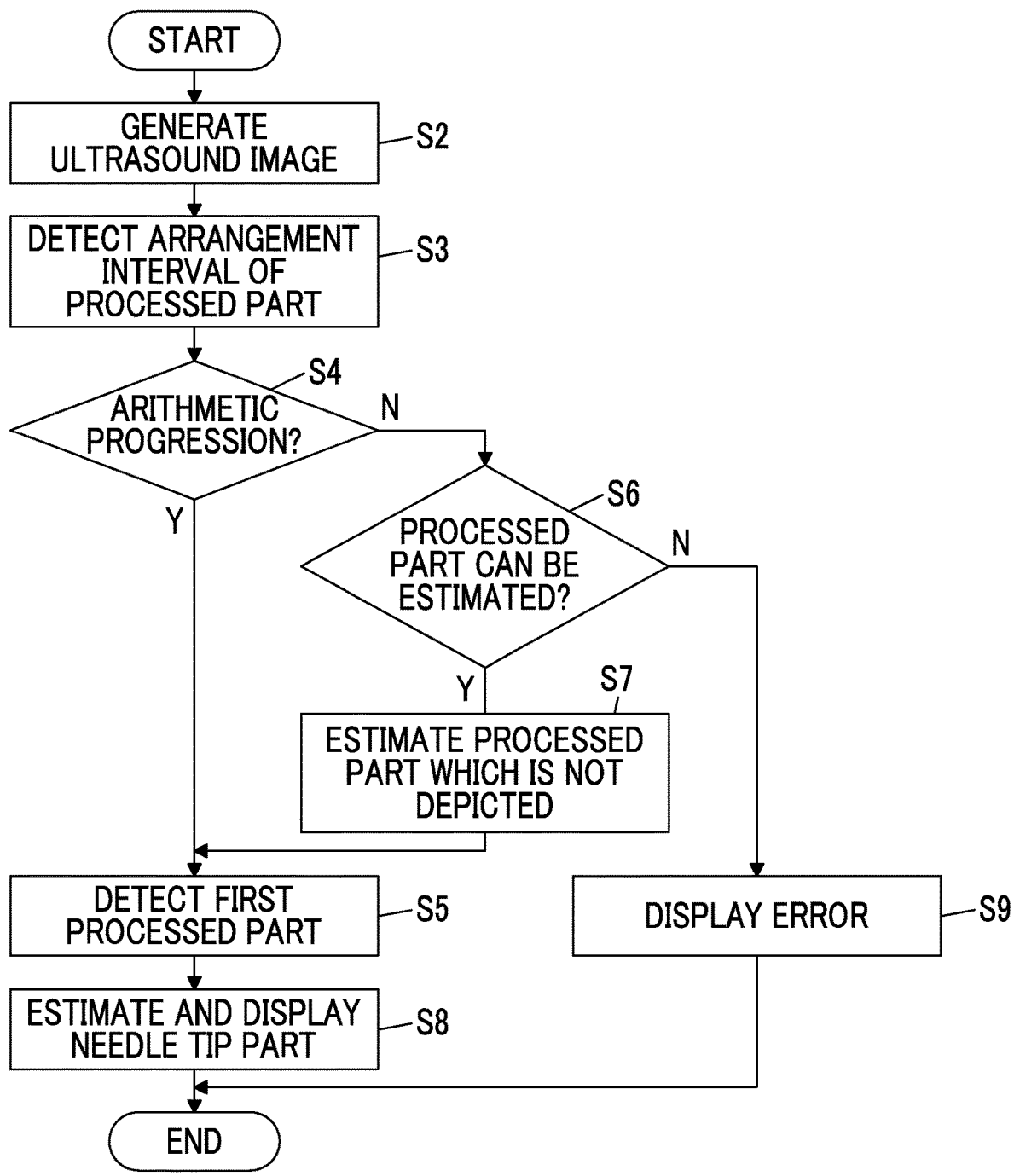
FIG. 11 is a flowchart showing an operation of an ultrasound diagnostic apparatus according to Embodiment 2 of the present invention.

Next, the operation of the ultrasound diagnostic apparatus 1 of estimating the position of the needle tip part T of the puncture needle N2 will be described with reference to the flowchart shown in FIG. 11.

First, in step S2, as in the aspect shown in FIG. 2, an ultrasound beam is applied from the ultrasound probe 2 in contact with the body surface B of the subject toward the puncture needle N2 in the subject, and an ultrasound image U is captured.

In step S3, the arrangement interval detection unit 9 recognizes the plurality of processed parts P1 to P5 of the puncture needle N2 and detects the arrangement intervals of the plurality of processed parts P1 to P5 by image analysis of the ultrasound image U generated in step S2.

In step S4, the arithmetic progression determination unit 10 determines whether or not the plurality of arrangement intervals detected in step S3 form an arithmetic progression. In a case where determination is made in step S4 that the plurality of arrangement intervals form an arithmetic progression, the process proceeds to step S5.

In step S5, the first processed part detection unit 11 calculates the tolerance of the arithmetic progression from the plurality of arrangement intervals detected in step S3, and specifies an arrangement interval which is larger than the calculated tolerance and equal to or less than twice the calculated tolerance as the arrangement interval L1 between the first processed part P1 and the second processed part P2 to detect the first processed part P1.

Here, in a case where an arrangement interval which is more than the tolerance and equal to or less than twice the tolerance is detected, an arrangement interval adjacent to the needle tip part T side of the puncture needle N2 from the detected arrangement interval is equal to or less than the tolerance, and thus it is equal to the distance L0 from the needle tip part T of the puncture needle N2 to the first processed part P1. Therefore, it is understood that an arrangement interval which is more than the tolerance and equal to or less than twice the tolerance is the arrangement interval L1 between the first processed part P1 closest to the needle tip part T and the second processed part P2 which is second closest to the needle tip part T. That is, the first processed part detection unit 11 can specify an arrangement interval which is more than the tolerance and equal to or less than twice the tolerance as the arrangement interval L1, and thereby, the first processed part P1 can be detected.

In a case where the first processed part P1 is detected in this way, the process proceeds to step S8.

In a case where determination is made in step S4 that the arithmetic progression is not formed by the plurality of arrangement intervals detected in step S3, the process proceeds to step S6.

In step S6, the arithmetic progression determination unit 10 determines whether or not the processed part which is not depicted in the ultrasound image U can be estimated. In a case where determination is made in step S6 that the processed part which is not depicted on the ultrasound image U can be estimated, the process proceeds to step S7.

In step S7, the first processed part detection unit 11 calculates the tolerance of the arithmetic progression from the plurality of arrangement intervals detected in step S3, and estimates the processed part which is not depicted in the ultrasound image using the calculated tolerance. In a case where the processed part which is not depicted in the ultrasound image U is estimated in this way, the process proceeds to step S5.

In step S5, the first processed part detection unit 11 detects the first processed part P1 by specifying an arrangement interval in which a value obtained by subtracting the tolerance calculated in step S7 from the arrangement interval is equal to or less than the tolerance as the arrangement interval L1 between the first processed part P1 and the second processed part P2 among the arrangement intervals of the plurality of processed parts P1 to P5 while taking into consideration the processed part estimated in step S7.

In step S8, the needle tip part position estimation unit 12 estimates, as a position of the needle tip part T, a point extending from the first processed part P1 detected in step S5 to a tip side of the shaft part S by a difference between the arrangement interval L1 between the first processed part P1 and the second processed part and the tolerance calculated in step S7 along the arrangement direction of the plurality of processed parts P1 to P5, that is, the length direction of the shaft part S of the puncture needle N2. Further, as in the aspect shown in FIG. 9, the needle tip part position estimation unit 12 superimposes a tip mark M representing the estimated position of the needle tip part T on the ultrasound image U generated in step S2 and displays the image on the display unit 7.

In a case where the process of step S8 is completed in this way, the operation of the ultrasound diagnostic apparatus 1 ends.

In addition, in step S6, in a case where the arithmetic progression determination unit 10 determines that the plurality of arrangement intervals detected in step S3 are not allowed to form an arithmetic progression and that a processed part which is not depicted in the ultrasound image U cannot be estimated, the process proceeds to step S9.

In step S9, the arithmetic progression determination unit 10 displays, although not shown, occurrence of an error on the display unit 7. In this way, in a case where the process of step S9 is completed, the operation of the ultrasound diagnostic apparatus 1 ends.

As described above, the puncture needle N2 according to Embodiment 2 of the present invention comprises the plurality of processed parts P1 to P5 forming an arithmetic progression in which values gradually decrease toward the needle tip part T, a distance K between the needle tip part T and the first processed part P1 is equal to or less than the tolerance of the arithmetic progression and equal to the difference between the arrangement interval between the first processed part P1 and the second processed part P2 and the tolerance. Therefore, the position of the needle tip part T is easily estimated by the ultrasound diagnostic apparatus 1 and displayed on the display unit 7. Thus, the user can accurately grasp the position of the needle tip part T of the puncture needle N2 as in the case of using the puncture needle N1 of Embodiment 1.

Embodiment 3

The ultrasound diagnostic apparatus 1 according to Embodiment 1 has a configuration in which the ultrasound probe 2 and the display unit 7 are directly connected to the processor 16, but for example, the ultrasound probe 2, the display unit 7, and the processor 16 can be indirectly connected to one another via a network.

Figure 12:
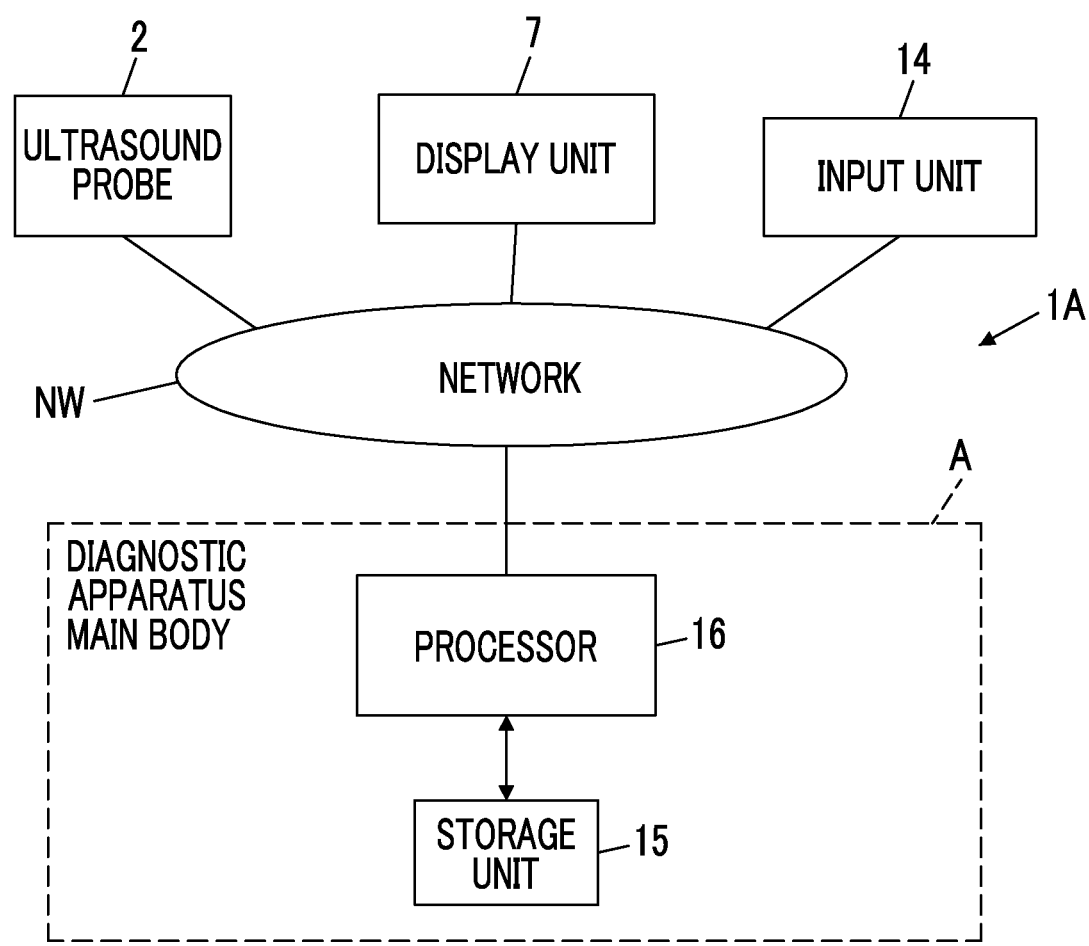
FIG. 12 is a block diagram showing a configuration of an ultrasound diagnostic apparatus according to Embodiment 3 of the present invention.

As shown in FIG. 12, in an ultrasound diagnostic apparatus 1A according to Embodiment 3, the ultrasound probe 2, the display unit 7, and the input unit 14 are connected to a diagnostic apparatus main body A via a network NW. The diagnostic apparatus main body A is the ultrasound diagnostic apparatus 1 shown in FIG. 3, excluding the ultrasound probe 2, the display unit 7, and the input unit 14.

Here, in a case where an ultrasound beam is transmitted from the ultrasound probe 2 toward the inside of the subject in a state where the ultrasound probe 2 is pressed against the body surface B of the subject by the user, an ultrasound echo reflected in the inside of the subject is received by the transducer array 2A of the ultrasound probe 2 to generate a reception signal. The ultrasound probe 2 transmits the generated reception signal to the diagnostic apparatus main body A via the network NW. The reception signal transmitted from the ultrasound probe 2 in this way is received by the image acquisition unit 8 of the processor 16 of the diagnostic apparatus main body A via the network NW, and the image acquisition unit 8 generates the ultrasound image U based on the reception signal.

The ultrasound image U generated by the image acquisition unit 8 is sent to the display control unit 6 and the arrangement interval detection unit 9. The display control unit 6 performs predetermined processing on the ultrasound image U received from the image acquisition unit 8, and further, transmits the ultrasound image U subjected to the predetermined processing to the display unit 7 via the network NW. In this way, the ultrasound image U transmitted from the display control unit 6 of the processor 16 of the diagnostic apparatus main body A is received by the display unit 7 via the network NW and displayed on the display unit 7.

The arrangement interval detection unit 9 recognizes the plurality of processed parts P1 to P7 of the puncture needle N1 and detects the arrangement intervals of the recognized plurality of processed parts P1 to P7 by image analysis of the ultrasound image U received from the image acquisition unit 8.

The arithmetic progression determination unit 10 determines whether or not the plurality of arrangement intervals detected by the arrangement interval detection unit 9 form an arithmetic progression, and the first processed part detection unit 11 detects the first processed part P1 of the puncture needle N1 based on a determination result by the arithmetic progression determination unit 10.

The needle tip part position estimation unit 12 estimates the position of the needle tip part T of the puncture needle N1 based on the position of the first processed part P1 detected by the first processed part detection unit 11 and the needle information input by the user via the input unit 14 and transmitted to the processor 16 of the diagnostic apparatus main body A via the network NW. Further, the needle tip part position estimation unit 12 superimposes information about the estimated position of the needle tip part T on the ultrasound image U and transmits the image to the display unit 7 via the network NW. Thus, the estimated position of the needle tip part T is displayed on the display unit 7.

As described above, according to the ultrasound diagnostic apparatus 1A according to Embodiment 3 of the present invention, even in a case where the ultrasound probe 2, the display unit 7, the input unit 14, and the diagnostic apparatus main body A are connected via the network NW, similarly to the ultrasound diagnostic apparatus 1 of Embodiment 1, the plurality of processed parts P1 to P7 are recognized to detect the arrangement intervals of the plurality of processed parts P1 to P7 by image analysis of the ultrasound image U, whether or not the detected plurality of arrangement intervals form an arithmetic progression is determined, a tolerance of the arithmetic progression is calculated, the first processed part P1 is detected based on the calculated tolerance, and the position of the needle tip part T is estimated based on the position of the detected first processed part P1. Therefore, the position of the needle tip part T can be estimated with high accuracy.

Since the ultrasound probe 2, the display unit 7, and the input unit 14 are connected to the diagnostic apparatus main body A via the network NW, the diagnostic apparatus main body A can be used as a so-called remote server. Thus, for example, the user can perform ultrasound diagnosis of the subject by preparing only the ultrasound probe 2, the display unit 7, and the input unit 14 at the user's hand, and thus convenience in the ultrasound diagnosis can be improved.

In addition, for example, in a case where a portable thin computer called a so-called tablet is used as the display unit 7 and the input unit 14, the user can more easily perform the ultrasound diagnosis of the subject, and convenience in the ultrasound diagnosis can be further improved.

Although the ultrasound probe 2, the display unit 7, and the input unit 14 are connected to the diagnostic apparatus main body A via the network NW, the ultrasound probe 2, the display unit 7, the input unit 14, and the diagnostic apparatus main body A may be wire-connected or wirelessly connected to the network NW.

Although it has been described that the aspect of Embodiment 3 is applied to Embodiment 1, the same can be applied to Embodiment 2.

| Explanation of References |
|---|
| 1, 1A: ultrasound diagnostic apparatus |
| 2: ultrasound probe |
| 2A: transducer array |
| 3: transmission unit |
| 4: reception unit |
| 5: image generation unit |
| 6: display control unit |
| 7: display unit |
| 8: image acquisition unit |
| 9: arrangement interval detection unit |
| 10: arithmetic progression determination unit |
| 11: first processed part detection unit |
| 12: needle tip part position estimation unit |
| 13: apparatus control unit |
| 14: input unit |
| 15: storage unit |
| 16: processor |
| 17: amplification unit |
| 18: AD conversion unit |

| Explanation of References |
|---|
| 19: signal processing unit |
| 20: DSC |
| 21: image processing unit |
| A: diagnostic apparatus main body |
| B: body surface |
| L0: distance |
| L1, L2, L25, L3, L35, L4, L5, L6: arrangement interval |
| M: tip mark |
| N1, N2: puncture needle |
| NW: network |
| P1: first processed part |
| P2: second processed part |
| P3: third processed part |
| P4: fourth processed part |
| P5: fifth processed part |
| P6: sixth processed part |
| P7: seventh processed part |
| S: shaft part |
| T: needle tip part |
| U: ultrasound image |

What is claimed is:

1. An ultrasound diagnostic apparatus comprising:
   a puncture needle comprising:
      a shaft part;
      a needle tip part disposed at a tip of the shaft part; and
      a plurality of processed parts that are arranged on an outer peripheral part of the shaft part along a length direction of the shaft part and form an arithmetic progression in which arrangement intervals gradually decrease toward the needle tip part,
      wherein among the plurality of processed parts, a first arrangement interval between a first processed part which is separated from the needle tip part by a predetermined distance and is closest to the needle tip part and a second processed part which is second closest to the needle tip part is less than a tolerance of the arithmetic progression, or
      the predetermined distance is equal to or less than the tolerance and equal to a difference between the first arrangement interval and the tolerance;
   a display device that displays an ultrasound image in which the puncture needle is captured; and
   a processor configured to:
      based on the ultrasound image, perform a process to recognize the plurality of processed parts of the puncture needle and detect the arrangement intervals of the recognized processed parts among the plurality of processed parts;
      determine whether or not the detected arrangement intervals of the plurality of processed parts form the arithmetic progression;
      calculate the tolerance of the arithmetic progression which is determined to be formed and detect the first processed part which is closest to the needle tip part among the plurality of processed parts based on the tolerance; and
      estimate a position of the needle tip part based on a position of the detected first processed part.

2. The ultrasound diagnostic apparatus according to claim 1,
   wherein the processor is further configured to:
      estimate a point extending from the first processed part to a tip side of the shaft part by the predetermined distance as the position of the needle tip part in a case where a first arrangement interval between the first processed part and the second processed part of the puncture needle is equal to or less than the tolerance of the arithmetic progression, and estimate a point extending from the first processed part to the tip side of the shaft part by the difference between the first arrangement interval and the tolerance as the position of the needle tip part in a case where the distance from the needle tip part to the first processed part of the puncture needle is equal to or less than the tolerance of the arithmetic progression and equal to the difference between the first arrangement interval and the tolerance.

3. The ultrasound diagnostic apparatus according to claim 1,
wherein the processor is further configured to display the estimated position of the needle tip part on the display device.

4. The ultrasound diagnostic apparatus according to claim 1, further comprising:
an ultrasound probe,
wherein the processor is further configured to acquire the ultrasound image by performing transmission and reception of an ultrasound beam between the ultrasound probe and a subject.

5. An ultrasound diagnostic apparatus comprising:
a puncture needle comprising:
a shaft part;
a needle tip part disposed at a tip of the shaft part; and
a plurality of processed parts that are arranged on an outer peripheral part of the shaft part along a length direction of the shaft part and form an arithmetic progression in which arrangement intervals gradually decrease toward the needle tip part,
wherein among the plurality of processed parts, a first arrangement interval between a first processed part which is separated from the needle tip part by a predetermined distance and is closest to the needle tip part and a second processed part which is second closest to the needle tip part is less than a tolerance of the arithmetic progression, or
the predetermined distance is equal to or less than the tolerance and equal to a difference between the first arrangement interval and the tolerance, and
wherein the plurality of processed parts are grooves formed to surround the outer peripheral part of the shaft part;
a display device that displays an ultrasound image in which the puncture needle is captured; and
a processor configured to:
based on the ultrasound image, perform a process to recognize the plurality of processed parts of the puncture needle and detect the arrangement intervals of the recognized processed parts among the plurality of processed parts;
determine whether or not the detected arrangement intervals of the plurality of processed parts form the arithmetic progression;
calculate the tolerance of the arithmetic progression which is determined to be formed and detect the first processed part which is closest to the needle tip part among the plurality of processed parts based on the tolerance; and
estimate a position of the needle tip part based on a position of the detected first processed part.

6. The ultrasound diagnostic apparatus according to claim 5,
wherein the processor is further configured to:

estimate a point extending from the first processed part to a tip side of the shaft part by the predetermined distance as the position of the needle tip part in a case where a first arrangement interval between the first processed part and the second processed part of the puncture needle is equal to or less than the tolerance of the arithmetic progression, and estimate a point extending from the first processed part to the tip side of the shaft part by the difference between the first arrangement interval and the tolerance as the position of the needle tip part in a case where the distance from the needle tip part to the first processed part of the puncture needle is equal to or less than the tolerance of the arithmetic progression and equal to the difference between the first arrangement interval and the tolerance.

7. The ultrasound diagnostic apparatus according to claim 5,
wherein the processor is further configured to display the estimated position of the needle tip part on the display device.

8. The ultrasound diagnostic apparatus according to claim 5, further comprising:
an ultrasound probe,
wherein the processor is further configured to acquire the ultrasound image by performing transmission and reception of an ultrasound beam between the ultrasound probe and a subject.

9. The ultrasound diagnostic apparatus according to claim 2,
wherein the processor is further configured to display the estimated position of the needle tip part on the display device.

10. The ultrasound diagnostic apparatus according to claim 2, further comprising:
an ultrasound probe,
wherein the processor is further configured to acquire the ultrasound image by performing transmission and reception of an ultrasound beam between the ultrasound probe and a subject.

11. The ultrasound diagnostic apparatus according to claim 6,
wherein the processor is further configured to display the estimated position of the needle tip part on the display device.

12. The ultrasound diagnostic apparatus according to claim 6, further comprising:
an ultrasound probe,
wherein the processor is further configured to acquire the ultrasound image by performing transmission and reception of an ultrasound beam between the ultrasound probe and a subject.

13. The ultrasound diagnostic apparatus according to claim 3, further comprising:
an ultrasound probe,
wherein the processor is further configured to acquire the ultrasound image by performing transmission and reception of an ultrasound beam between the ultrasound probe and a subject.

14. The ultrasound diagnostic apparatus according to claim 7, further comprising:
an ultrasound probe,
wherein the processor is further configured to acquire the ultrasound image by performing transmission and reception of an ultrasound beam between the ultrasound probe and a subject.

15. The ultrasound diagnostic apparatus according to claim 9, further comprising:
an ultrasound probe,
wherein the processor is further configured to acquire the ultrasound image by performing transmission and reception of an ultrasound beam between the ultrasound probe and a subject.

16. The ultrasound diagnostic apparatus according to claim 11, further comprising:
an ultrasound probe,
wherein the processor is further configured to acquire the ultrasound image by performing transmission and reception of an ultrasound beam between the ultrasound probe and a subject.

* * * * *